United States Patent [19]

Tanner

[11] Patent Number: 4,537,193
[45] Date of Patent: Aug. 27, 1985

[54] LASER ENDOCOAGULATOR APPARATUS

[75] Inventor: Howard M. C. Tanner, Salt Lake City, Utah

[73] Assignee: HGM, Inc., Salt Lake City, Utah

[21] Appl. No.: 437,288

[22] Filed: Oct. 28, 1982

[51] Int. Cl.³ .................. A61B 17/36; A61N 5/00
[52] U.S. Cl. .................. 128/303.1; 128/398; 350/96.20
[58] Field of Search .................. 128/303.1, 395–398; 219/121 L, 121 LP, 121 LQ, 121 LR; 350/96.20; 372/108

[56] References Cited

U.S. PATENT DOCUMENTS

| 3,383,491 | 5/1968 | Muncheryan | 219/121 LR |
| 3,471,215 | 10/1969 | Snitzer | 350/96 |
| 3,538,919 | 11/1970 | Meyer | 128/398 |
| 3,693,623 | 9/1972 | Harte et al. | 128/303.1 |
| 3,746,814 | 7/1973 | Lackey et al. | 200/157 |
| 3,821,510 | 6/1974 | Muncheryan | 219/121 L |
| 3,825,004 | 7/1974 | Durden, III | 128/275.1 |
| 3,834,391 | 9/1974 | Block | 128/303.1 |
| 3,865,113 | 2/1975 | Sharon et al. | 128/303.1 |
| 3,910,278 | 10/1975 | Crandell et al. | 128/303.1 |
| 3,982,541 | 9/1976 | L'Esperance, Jr. | 128/303.1 |
| 4,034,761 | 7/1977 | Prater et al. | 128/303.14 |
| 4,126,136 | 11/1978 | Auth et al. | 128/303.1 |
| 4,233,493 | 11/1982 | Nath | 219/354 |
| 4,316,467 | 2/1982 | Muckerheide | 128/303.1 |

FOREIGN PATENT DOCUMENTS

| 2740969 | 3/1979 | Fed. Rep. of Germany | 128/398 |
| 2828322 | 1/1980 | Fed. Rep. of Germany | 128/303.1 |
| 2479485 | 10/1981 | France | 128/303.1 |

OTHER PUBLICATIONS

Smith et al., "New Trends in $CO_2$ Laser Micro. . . . ", SPIE, vol. 236, 1980, pp. 173–182.

Primary Examiner—Lee S. Cohen
Attorney, Agent, or Firm—B. B. Olive

[57] ABSTRACT

A disposable laser endocoagulator apparatus for ophthalmic surgery or the like. The apparatus includes an elongated, generally pencil-like handtool which has a stainless steel probe positioned at the leading end of the handtool. An optical fiber is inserted through a bore in the handtool such that the optical fiber terminates at the distal end of the probe. The optical fiber is attached to a connector which includes a plastic body, the plastic body having a small metal plug inserted into it. The metal plug is constructed of stainless steel so as to be capable of being machined with great precision such that the optical fiber carried by the plug can be accurately positioned and aligned with respect to the laser beam output by a conventional argon ion type laser.

2 Claims, 2 Drawing Figures

LASER ENDOCOAGULATOR APPARATUS

BACKGROUND

1. The Field of the Invention

The present invention relates to laser apparatus used for purposes of surgery and, more particularly, to a disposable laser endocoagulator apparatus for ophthalmic surgery.

2. The Prior Art

The advent of the laser has opened new frontiers to many areas of science and has revolutionized many procedures. One of the most important of these new frontiers has been the application of laser technology to various procedures in the field of medicine. Because lasers can be focused onto very small areas, it is possible to be very precise and to treat specific pathologies without affecting surrounding tissue.

The first significant medical use of a laser occurred in 1965 when doctors utilized a laser to repair a detached retina. The surgeons were able to focus the laser into the interior portion of the eyeball and "weld" the detached retina back into place. At the point where the laser beam struck the retina, the light energy was converted into heat energy which produced a coagulum. During the next few weeks, this coagulum was converted to scar tissue which anchored the retina in place. Since that time, the procedure has been much improved and the utilization of lasers has become a generally accepted method of repair in this type of abnormality. Surgical laser apparatus has also been used to repair retinal tears and abnormal blood vessels within the eye.

Notwithstanding the substantial advances in ophthalmic surgery which have come about as a result of the improvements in laser technology, the current state of the art leaves much to be desired. For example, in the past it has been common practice to use xenon lasers for purposes of ophthalmic surgery. The laser beam from a xenon laser has a tendency to scatter to a certain degree, thus losing some of its intensity and precision. Because of this tendency, the tip of the optical fiber through which the laser beam passes must almost be in contact with the eye tissue which is being treated. Since ophthalmic surgery is typically conducted in the dark so that only the area of the eye on which the surgery is occurring is illuminated, this increases the possibility of causing additional damage to the eye because the surgeon, in attempting to place the tip of the optical fiber so that it is almost in contact with the eye tissue, may accidentally touch the tissue causing a further tear or causing physical damage to surrounding tissue.

The laser endocoagulators used for ophthalmic surgery have typically been rather complicated in their structure. For example, typically the handtool of a laser endocoagulator is quite expensive in its construction because it is made entirely from stainless steel. Thus, the practice in the art has been to resterilize the entire endocoagulator so that it can be reused time after time. However, not only are such resterilization techniques time consuming and expensive in terms of additional labor and handling, but it also renders it more difficult to maintain the delicate optical fiber of the endocoagulator in top condition. For example, it is important that the end of the optical fiber be polished and free from debris so that the laser beam will be transmitted without interference. Any irregularity in the tip of the optical fiber may cause a portion of the light to be absorbed, thus decreasing the amount of the light transmitted causing the tip of the fiber to become overheated, as well as degrading the quality of the laser beam omitted from the tip of the fiber.

Additionally, the connectors utilized to attach the optical fiber to the laser source have generally consisted of a number of very carefully machined metal parts adapted to fit together with great precision so as to accurately align the optical fiber with the laser beam. If the laser beam is not properly aligned with the end of the optical fiber, much of its power can be lost. Additionally, the misdirected beam can vaporize portions of the connector, thus destroying it or creating debris which can obscure the end of the fiber.

Some of the connectors used in the prior art have incorporated a series of lenses to focus the laser beam onto the end of the optical fiber. Many prior art type connectors also incorporate a convex, gold collar disposed about the end of the optical fiber so as to provide an inert reflective surface for the laser beam in the event that it is not precisely aligned with the end of the optical fiber.

While these prior art connectors have proven effective, they are disadvantageous for several reasons. First, such connectors are very expensive to manufacture because of the number of parts that must be carefully machined so as to fit together within extremely close tolerances. While this disadvantage is partially offset by the fact that the connectors are reusable, this creates a second problem. The optical fiber held between the probe and the connector is typically in need of repair or replacement after only a few surgical operations. Because of the need for extremely precise positioning of the optical fiber within the endocoagulator and its connector, it has heretofore been necessary to send the entire assembly back to the factory for repair or replacement. Since the time required for these repairs is generally several weeks, it has proven necessary for hospitals performing large numbers of ophthalmic operations to have many endocoagulator assemblies in their inventory. This requires a large capital outlay and significant inventory cost.

Another problem associated with prior art laser endocoagulators is the need to insure that they are absolutely sterile before reuse. Inasmuch as the tip of the probe is inserted within the eye, extreme care must be taken to insure that the probe is completely sterile to prevent the introduction of bacteria.

Thus, what is needed in the art is a laser endocoagulator apparatus which is very simple in its construction and which is economical to manufacture so that it can be easily disposed of after a single use, and which effectively overcomes the disadvantages of the prior art type endocoagulators mentioned above.

OBJECTS AND BRIEF SUMMARY OF THE INVENTION

It is a primary object of the present invention to provide a laser endocoagulator apparatus which is relatively simple in its construction and which is inexpensive to manufacture so that it can be utilized once and discarded.

It is a further object of this invention to provide a laser endocoagulator apparatus which includes a simple and inexpensive connector which insures that the optical fiber is precisely aligned with the output of the laser source.

Another object of the present invention is to provide an endocoagulator apparatus for use with an argon ion laser so as to provide greater precision in the use of the laser beam.

These and other objects and features of the present invention will become more fully apparent from the following description and appended claims taken in conjunction with the accompanying drawings.

In accordance with the foregoing objects, the present invention provides a novel laser endocoagulator apparatus suitable for use in ophthalmic surgery. The entire apparatus is inexpensive to manufacture and thus disposable.

In the presently preferred embodiment, the laser endocoagulator apparatus of the present invention includes an elongated handtool constructed of plastic. The end of the handtool is slightly tapered and a stainless steel probe projects from the end thereof. A silicon clad optical fiber passes through the center of the handtool and the fiber terminates at the end of the probe. A series of circular grooves are formed on the forward portion of the handtool to facilitate its handling. A two-piece disposable connector is attached to the other end of the optical fiber for attaching the fiber to a laser source. The connector includes a cylindrical plastic body having a bore passing through the center thereof into which the optical fiber is anchored. A small metal plug, machined to the necessary tolerance, is positioned in the terminal end of the plastic body for precisely aligning the tip of the optical fiber with the output of the laser source.

BRIEF DESCRIPTION OF THE DRAWINGS

Reference is next made to the drawings, in which like parts are designated with like numerals throughout, and in which.

DETAILED DESCRIPTION OF THE PREFERRED EMBODIMENTS

Figure 1:
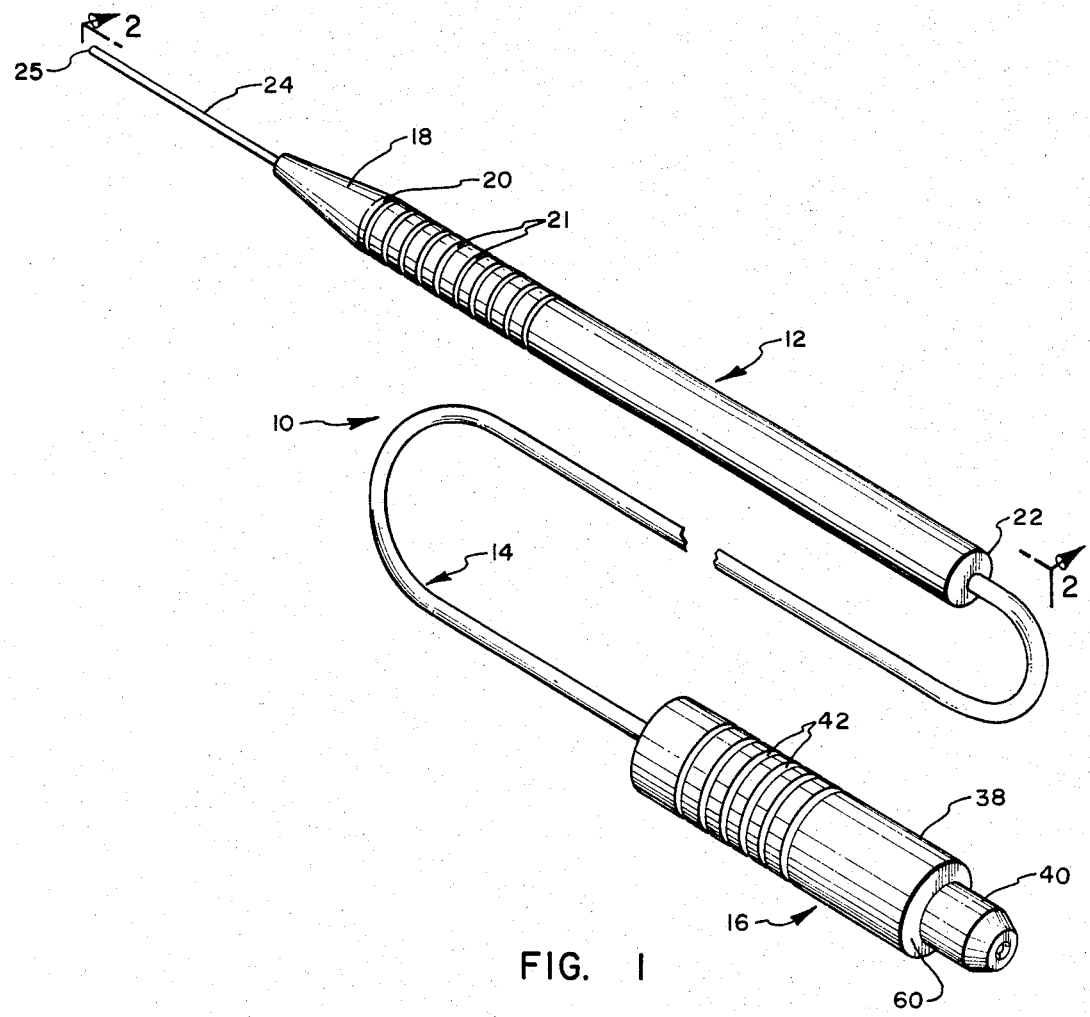
FIG. 1 is a perspective view of the handtool, optical fiber and connector forming the endocoagulator apparatus of the present invention.

Referring first to FIG. 1, the laser endocoagulator apparatus of the present invention is generally designated at 10. The apparatus 10 includes an elongated, generally pencil-like handtool which is generally designated at 12, a length of optical fiber generally designated at 14 which is connected at one end to the handtool 12, and which is connected at the other end to a cylindrically shaped connector generally designated at 16. The handtool is tapered to a point at its forward end 18.

On performing ophthalmic surgery, it is of utmost importance to exercise great care so as to insure precision and accuracy in inserting and positioning the probe within the interior regions of the eye. Thus, the handtool 12 is slightly tapered along its body from the leading end 20 back to the trailing end 22. Also, the leading end 20 of the body is provided with a plurality of annular grooves 21 which facilitate gripping and handling of the handtool with a greater degree of precision and accuracy. The slender, tapered, pencil-like shape of handtool 12 is specifically designed to meet the needs of ophthalmic surgeons so as to facilitate handling and precision in using the instrument.

The handtool 12 is, in the preferred embodiment, constructed as an integral piece using conventional injection molding techniques or the like. Handtool 12 is typically made from ABS (acrylonitrile butadiene styrene) plastic material or other similar material so as to be economical, lending to disposability of the handtool after its use. Also, in the preferred embodiment the handtool 12 is constructed from a plastic material which has a generally grey, flat, dull finish. Since ophthalmic surgeons typically must operate in the environment of an almost totally dark operating room, it is desirable to avoid using instruments which are light colored or which may be highly reflective and which might thus detract from the field of surgery.

A stainless steel, medical grade probe in the form of a thin, elongated tube 24 is anchored to the tip 18 of handtool 12. As hereinafter more fully described, probe 24 carries inside of it the optical fiber through which the laser beam is transmitted. Typically, the probe 24 is inserted into the interior regions of the eye through a small incision.

Figure 2:
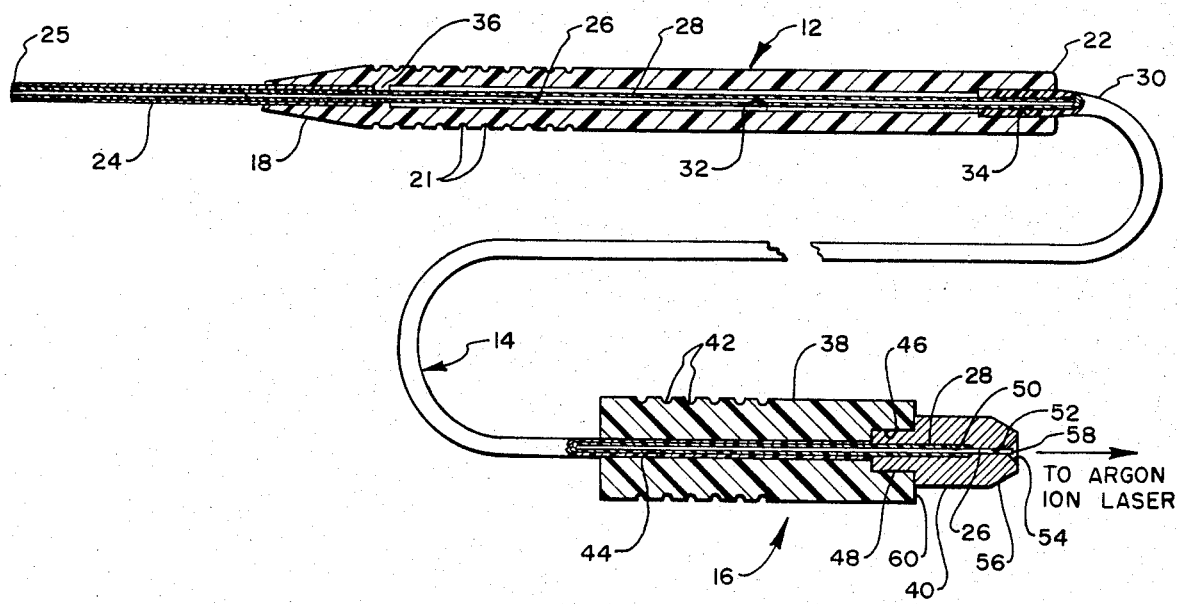
FIG. 2 is a longitudinal cross-sectional view of the handtool and connector taken along line 2—2 of FIG. 1.

With reference next to FIG. 2, it will be seen that the optical fiber generally designated at 14 includes a small quartz fiber 26 through which the laser beam is optically transmitted to the leading tip 25 of the metal probe 24. The leading end of the quartz fiber 26 is inserted through the probe 24 to a point just slightly beyond the tip of the probe 24. The end of the quartz fiber is then polished to remove debris such as excess adhesive or the like which may be attached to the tip of the quartz fiber 26 during assembly procedures. Since the quartz fiber 26 is typically very small (on the order of 400 microns), except for its leading end the quartz fiber 26 is encased in a silicon sheath 28 which enhances the optical transmission properties of fiber 26, and which also lends structural support to the quartz fiber 26 and protects it from being damaged. In some cases, an additional layer (not shown) of Tefzel (TM) may be used to give further strength to the quartz fiber 26. The silicon clad quartz fiber is commonly referred to as a "dressed optical fiber," and is commercially available from one of several companies. For example, in the illustrated embodiment the dressed optical fiber is a black fiber which is advantageous for use in the context of ophthalmic surgery because it inhibits transmission of light except at the tip of the probe, which fiber may be obtained from Quartz Products Company of Plainfield, N.J.

The dressed optical fiber consisting of silicon sheath 28 and quartz fiber 26 is further encased in a flexible plastic tube 30 which protects the portion of the fiber which leads from the handtool 12 to the connector 16. Tubing 30 can be constructed of polyethylene or polypropylene plastic or other suitable material.

As shown best in FIG. 2, the optical fiber 14 is inserted through the interior of the handtool 12 by means of an interior bore 32 which extends through the center of the handtool 12. At one end 34 the bore is diametrally enlarged for purposes of receiving the plastic tubing 30, which is bonded or otherwise anchored to trailing end 22 of the handtool 12. At the other end of bore 32, an annular shoulder 36 is formed so as to reduce the diameter of the bore. The annular shoulder 36 defines the farthest point at which the metal probe 24 may be inserted into the tapered end 18 of handtool 12. The inside diameter of the metal probe 24 and the reduced diameter defined by annular shoulder 36 correspond in size to the outside diameter of the sheath 28 encasing quartz fiber 26, whereas the inside diameter of the bore 32 is sized to accept the outside diameter of the silicon sheath 28 which is used for purposes of encasing the quartz fiber 26. The optical fiber may be suitably bonded or otherwise secured inside the bore 32 and metal probe 24.

As schematically illustrated in FIG. 2, the laser endocoagulator of the present invention is adapted to be connected by means of the connector 16 to a conventional laser source, which, in the preferred embodiment, may be an argon ion type laser manufactured by American Laser Corporation in Salt Lake City, Utah. Argon lasers produce a visible blue-green light having a wavelength in the 488 to 514 nanometer range. This light is easily transmitted through clear aqueous tissue such as the cornea, lens, and vitreous humor of the eye. On the other hand, certain tissue pigments such as melanin and hemoglobin absorb the light omitted by an argon laser very effectively. Thus, an argon laser is very effective, even more so than a xenon laser, when used for purposes of endocoagulation in ophthalmic surgery.

The connector 16 is configurated as a male fitting which is designed to be received by a corresponding female socket (not shown) provided in the argon laser. Connector 16 includes a cylindrical body 38 which is constructed of a rigid plastic material so as to be inexpensive and easily manufactured using conventional molding technology. The exterior surface of connector 16 is provided with a plurality of annular grooves 42 which permit the connector 16 to be securely grasped when inserting or removing the connector 16 from the corresponding socket of the laser.

As illustrated in FIG. 2, the body 38 of connector 16 has an enlarged bore 46 formed in one end thereof which in turn communicates with a diametrally reduced bore 44 which extends through the remaining length of the body 38. Bore 44 is adapted to receive the protective tubing 30 which surrounds the optical fiber.

As mentioned above, it is essential that the quartz fiber 26 be precisely aligned with the laser beam which is output from the laser source. Because it is difficult to manufacture plastic connectors within the necessary degree of tolerance required to assure the needed alignment, the current practice in the art is to construct the connectors entirely out of high precision, machined steel components which, in some cases, go so far as to include special lenses or reflecting apparatus to insure focusing of the laser beam onto the exposed tip of the quartz fiber. The apparatus of the present invention seeks to overcome the disadvantages which are inherent in the use of these kinds of expensive and complicated connecting apparatus by providing a connector which is simple and inexpensive in its overall construction, but which does not sacrifice the needed precision in terms of alignment.

As shown in FIG. 2, a small metal plug 40 is joined to the plastic body 38 of the connector. Plug 40 is made from stainless steel so that it can be machined within extremely close tolerances, thus insuring precise alignment of the optical fiber positioned in the plug with the laser beam output by the laser.

Obviously, materials other than plastic and metal could be used for the body 38 and plug 40 of connector 16. For example, it may be possible to form the plug 40 out of some types of plastic where the particular type of plastic can be machined or otherwise formed within the necessary tolerance to insure proper alignmment, in which case the body 38 and plug 40 could be formed either as an integral, one-piece connector, or in two pieces as illustrated. The dominant considerations in choosing the particular materials for body 38 and plug 40 are to select a material, like plastic, which can be used for the body portion so as to minimize expense, thus lending to disposability, and to select a material, like stainless steel, which can be used for the smaller plug portion and which can be machined with great precision to insure proper alignment of the optical fiber with the laser beam. Thus, use of the terms "plastic" and "metal" is not intended to be a limitation on the scope of the invention, but is instead intended to be representative of the foregoing design considerations.

Plug 40 includes an annular extension 48 which is adapted to be received by the diametrally enlarged bore 46 formed in the end of the plastic body 38. The tip of plug 40 is chamfered as at 56 to facilitate insertion of the plug 40 into the corresponding socket of the laser. A through bore 50 is formed through the center of the plug 40 along a portion of its length. The inside diameter of bore 50 corresponds to the outside diameter of the silicon sheath 28 which surrounds the quartz fiber 26. The silicon sheath 28 is stripped from the end 58 of quartz fiber 26, which then projects through the diametrally reduced bore 52 located in the end portion of plug 40.

The tip of plug 40 also includes a conical recess 54 into which the tip 58 the of quartz fiber 26 extends a short distance so as to be entirely exposed to the laser beam output by the laser source. The tip 58 of the optical fiber is preferably recessed slightly within cavity 54 so that it cannot be damaged during storage or handling. The length of plug 40 is designed such that the end 60 of the plastic body 38 will abut against the female socket into which the plug 40 is inserted.

In summary, from the foregoing description and drawings it will be appreciated that the endocoagulator apparatus of the present invention may be efficiently and economically constructed largely using plastic materials which may be easily manufactured using conventional molding technology and thus lending to disposability of the entire apparatus after a single use. The laser endocoagulator of this invention advantageously provides for easier handling and greater precision in using the laser beam for purposes of ophthalmic surgery.

Although the present invention has been described with reference to its presently preferred embodiment, the invention may be embodied in other specific forms without departing from the spirit or essential characteristics thereof. The described embodiment is to be considered in all respects only as illustrative and not restrictive, and the scope of the invention is, therefore, indicated by the appended claims rather than by the foregoing description. All modifications or changes which come within the meaning and range of equivalency of the claims are to be embraced within their scope.

What is claimed and desired to be secured by United States Letters Patent is:

1. A disposable endocoagulator apparatus adapted for connection to an argon laser having a female receptacle providing a laser output suited to optical fiber transmission for ophthalmic surgery and like procedures, comprising:
    (a) an elongated, cylindrical-shaped handtool formed as a integral, plastic molded structure having:
        (i) a cylindrical, pencil-like body having a leading end and a trailing end;

(ii) a tip portion formed integral with said body leading end and tapered towards the leading end of said body;

(iii) a central bore extending through the length of said handtool body and tip portion;

(iv) within said tip portion a first enlarged bore concentric with said central bore for mounting a probe;

(v) within the trailing end of said body a second enlarged bore concentric with said central bore for receiving a first optical fiber sheath; and (vi) within said body an annular shoulder surrounding and concentric with said central bore and extending within said body between said shoulder and said second enlarged bore a third enlarged bore substantially equal in size to the size of said first enlarged bore and concentric with said central bore for receiving a second optical fiber sheath;

(b) a hollow, elongated, stainless steel tube forming a laser probe, said probe having a minor portion of the length thereof anchored in said tip portion first enlarged bore and having a major portion of the length thereof extending outwardly from said tip portion to a leading end, the axis of said probe being aligned with the axis of said handtool;

(c) a fiber optics connector assembly comprising:

(i) an elongated, cylindrical-shaped, integral, plastic-molded body member having a leading end and a trailing end and having a central bore through the length thereof and a fourth enlarged bore at the trailing end thereof concentric with said body member central bore, said body member having a flat annular surface at the trailing end thereof surrounding said body member fourth enlarged bore; and (ii) a cylindrical, precisely-formed, male plug member having a leading end and a trailing end and positioned at the trailing end of and forming an integral connector structure with said body member, said plug member having a cylindrical portion of reduced diameter at its leading end and being secured to said body member by said plug member leading end of reduced diameter being inserted and secured in said body member fourth enlarged bore, the trailing end of said plug member being tapered for guiding said male plug member into said female receptacle, said plug member having a bore aligned with and forming a continuation of the central bore of said body member and at the trailing end of said plug member an inwardly tapered recess around the plug member bore, the diameter and length of said male plug member being adapted for precise alignment and positioning within a mating argon laser female receptacle having an output source oriented along an axis aligned with the axis of said male plug member when inserted in said female receptacle, said flat annular surface serving as a stop for controlling the depth of said plug member in said receptacle; and (d) a single, continuous length of optical fiber, said optical fiber having:

(i) a leading portion extending from a leading polished end surface positioned slightly outwardly from the leading end of said probe and extending through said probe and handtool bore;

(ii) an intermediate portion extending from the trailing end of said handtool to said connector assembly;

(iii) a trailing end portion extending through said connector assembly body member central bore and said plug member bore and terminating with a trailing end surface disposed slightly within said plug member recess;

(iv) a first cladding sheath extending over said length of optical fiber from a location slightly behind the leading polished end thereof to a location within said plug member and forwardly of said recess; and (v) a second plastic sheath anchored in said connector assembly body member central bore at one end and surrounding said optical fiber and extending to and anchored in said second enlarged bore at the trailing end of said handtool.

2. A disposable endocoagulator apparatus as claimed in claim 1 wherein said plug member is formed of a precision machined metal.

* * * * *